United States Patent [19]
Chinn, Jr. et al.

[11] Patent Number: 5,965,803
[45] Date of Patent: Oct. 12, 1999

[54] ODOR COLLECTION APPARATUS

[75] Inventors: John W. Chinn, Jr., Plantsville, Conn.; Tetsuo Nakatsu, Chappaqua, N.Y.

[73] Assignees: Takasago International Corporation, Japan; Takasago Institute for Interdisciplinary Science, Inc., Rockleigh, N.J.

[21] Appl. No.: 08/965,169

[22] Filed: Nov. 6, 1997

[51] Int. Cl.$^6$ .............................. G01N 7/00; G01N 1/00; B01L 3/00
[52] U.S. Cl. ................. 73/23.34; 73/863.21; 73/864.91; 73/31.07
[58] Field of Search .............................. 73/23.24, 863.21, 73/864.91, 31.07, 23.41

[56] References Cited

U.S. PATENT DOCUMENTS

| | | | |
|---|---|---|---|
| 4,102,201 | 7/1978 | Trine et al. | 73/863.21 |
| 4,615,468 | 10/1986 | Gay | 73/864.91 |
| 5,136,805 | 8/1992 | Mookherjee | 73/23.34 |
| 5,369,978 | 12/1994 | Mookherjee et al. | 73/23.34 |

*Primary Examiner*—Hezron Williams
*Assistant Examiner*—Chad Soliz
*Attorney, Agent, or Firm*—Morrison Law Firm

[57] ABSTRACT

An adsorbent coating is affixed to the internal wall of a sealable container. The container may be rigid or flexible. The adsorbent coating, when in the sealed container retains odor components for an extended period permitting the odor components to be transported without requiring the transport of the source of the components. Thermal, or other desorption techniques release the odor components for analysis by, for example, liquid chromatography or gas chromatography. One embodiment of the invention is disclosed in which the container is a flexible bag, coated on its interior with an adsorbent material. In another embodiment of the invention, a large surface-area body, containing sorbent material on its surfaces, is contained within the container.

13 Claims, 3 Drawing Sheets

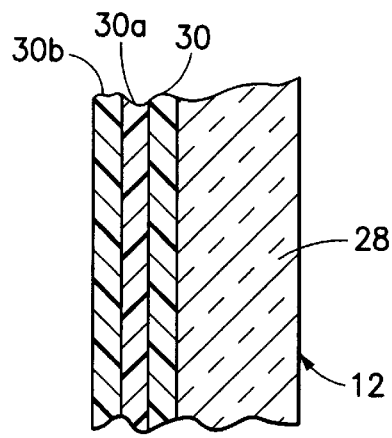
FIG.4
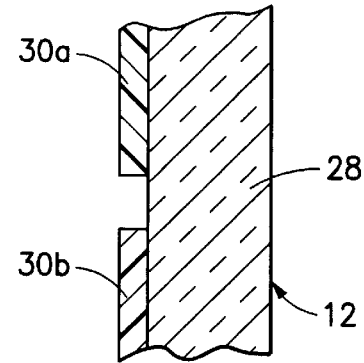
FIG.5
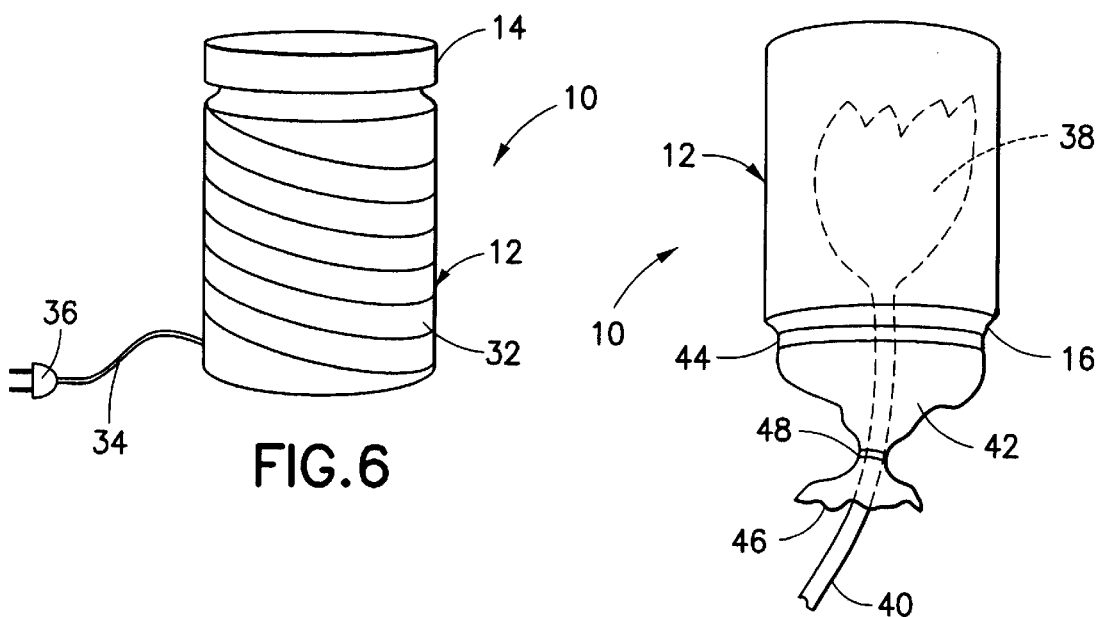

ODOR COLLECTION APPARATUS

BACKGROUND

The present invention relates to odor collection and analysis and, more particularly, to apparatus for collecting large odor samples and for storing the odor samples for an extended period before analysis.

The analysis of odor components is complicated by the small quantities of volatile components in the headspace of an object whose odor is to be collected and analyzed. The amounts are generally in the sub-microgram range. Thus, some method of concentrating the odor components over a period of time is desirable. One method of concentrating the odor components includes drawing air, or an inert carrier gas such as nitrogen or hydrogen over the object and passing the gas containing the odor components through an adsorptive material such as Tenax. Normal laboratory procedures also include removal from the gas stream of water vapor using a cold trap or a water absorbent such as $CaCl_2$ and a suitable trap for carbon dioxide. The odor components adsorbed in the adsorptive material is desorbed and analyzed by conventional gas or liquid chromatography.

Another prior art device for odor collection and analysis consists of a fused silica fiber coated with an adsorptive material that adsorbs odor components either directly from the headspace of an object or from the air space of an object confined in a container. The fiber is then heated to desorb the components, which may be analyzed by conventional gas chromatography. The same device can also be used to adsorb organic components from a solution. The adsorbed species then can be either thermally desorbed for analysis by gas chromatography or solvent desorbed for analysis by conventional liquid chromatography. In both cases the main deficiency of the silica fiber device is its limited sample capacity (in the nanogram range of amounts).

Another device uses a "plastic" bag to enclose an object (e.g., a flower) whose odor is to be collected for a period long enough to obtain measurable levels of odor components. The object is removed from the bag, and the bag is squeezed to expel odor components into an adsorbent material such as Tenax. The adsorbed components then can be desorbed for analysis by gas or liquid chromatography.

The bag technique has four principal disadvantages when it is employed in the field to capture odor components. First, many types of plastic used for this purpose may be at least slightly permeable, thereby permitting loss of some odor components or infiltration of outside contaminants, or both. Second, the polymer may contaminate the odor components with outgassed components of its own. Third, since the bag must be large enough to contain the entire object, there is a size and portability problem when it is desired to collect a large number of samples of odors in a field trip. Finally, it is often desirable to return the bag with its contained object to the laboratory for multiple analyses. This becomes a difficult to impossible task when it is necessary to transport bagged samples across national boundaries.

Although the preceding and ensuing disclosure uses the words "odor components" to describe the techniques being employed, it must be understood that the invention is not limited to collection and analysis of odors. The invention must be seen as relating to collection and storage of any chemical component, and the delivery of that component for analysis, whether or not such chemical component is an olfactory stimulant. The present disclosure is cast in the environment of gaseous components. However, the apparatus and methods discussed herein are equally applicable to sorption of chemical components from a liquid, and also to desorption into a liquid medium which may then be subjected to analysis using, for example, liquid chromatography.

OBJECTS AND SUMMARY

It is an object of the invention to provide an odor collection device which overcomes the drawbacks of the prior art.

It is a further object of the invention to provide an odor collection device which permits relatively long-term storage of an odor.

It is a still further object of the invention to provide an odor collection device which stores an odor and delivers the odor components for analysis at a location remote from the location at which the sample is collected.

Briefly stated, the present invention provides an odor storage medium in which an adsorbent coating is affixed to the internal wall of a sealable container. The container may be rigid or flexible. The adsorbent coating, when in the sealed container retains odor components for an extended period, permitting the odor components to be transported without requiring the transport of the source of the components. Thermal, or other desorption techniques release the odor components for analysis by, for example, liquid chromatography or gas chromatography. One embodiment of the invention is disclosed in which the container is a flexible bag, coated on its interior with an adsorbent material. In another embodiment of the invention, a large surface-area body, containing sorbent material on its surfaces, is contained within the container.

According to an embodiment of the invention, there is provided apparatus for collecting odor components, comprising: a container, means for sealing the container, a sorbent coating on an interior surface of the container, the sorbent coating being of a type effective for sorbing odor components, and the container having a capacity sufficient to contain a source of the odor components for a period of time long enough for the odor components to reach equilibrium within the container.

According to a feature of the invention, there is provided apparatus for collecting odor components, comprising: a flexible container, a rigid container into which the flexible container can be inserted, means for conforming the flexible container closely to an interior of the rigid container, a sorbent coating on an interior surface of the flexible container, and means for heating the rigid container while the flexible container is conformed thereto, whereby the odor components in the sorbent coating may be desorbed within a predetermined time.

According to a further feature of the invention, there is provided a method for coating a sorbent material on an interior surface of a generally cylindrical rigid container, comprising: mixing a predetermined first amount of a polymer sorbent material in a second amount solvent to produce a diluted material, placing a quantity of the diluted material into the cylindrical container, rolling the cylindrical container in a roll mill with its axis generally horizontal until the solvent evaporates, and the first amount being sufficient to produce a resultant polymer coating on an interior surface of the cylindrical container of between 1 and 1,000 micrometers, after evaporation of the solvent.

According to a still further feature of the invention, there is provided a method for coating a sorbent material on an interior of a flexible container comprising: vacuum conforming the flexible container to an interior of a generally cylindrical rigid container, mixing a predetermined first amount of a polymer sorbent material in a second amount solvent to produce a diluted material, placing a quantity of the diluted material into the flexible container, rolling the rigid container, with the flexible container conformed to its interior in a roll mill with its axis generally horizontal until the solvent evaporates, and the first amount being sufficient to produce a resultant polymer coating on an interior surface of the flexible container of between 1 and 1,000 micrometers, after evaporation of the solvent.

According to another feature of the invention, there is provided a method for desorbing odor components sorbed in a sorbent coating in an interior of a flexible container, comprising: vacuum conforming the flexible container to an interior of a rigid container, and heating an interior surface of the rigid container, whereby heat is transferred through the flexible container to the sorbent material therein.

According to a still further feature of the invention, there is provided apparatus for collecting odor components, comprising: a container, means for sealing said container, a large surface-area body within said container, a sorbent coating on said large surface-area body, said sorbent coating being of a type effective for sorbing odor components, and said container having a capacity sufficient to contain a source of said odor components for a period of time long enough for said odor components to reach equilibrium with sorbent material within said container.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 4 is an alternate cross section taken along III—III of FIG. 1, wherein a plurality of layers of adsorbent materials are built up on the substrate.

FIG. 5 is a further alternate cross section taken along III—III of FIG. 1, wherein side-by-side zones of different adsorbent materials provide for adsorbence of different components.

FIG. 6 is a perspective view of the odor collection apparatus of FIG. 1 wherein a heating tape is wound thereon to enable thermal desorption of collected components.

FIG. 7 is a side view of an odor collection apparatus during collection of odor components from a living blossom.

DETAILED DESCRIPTION OF THE PREFERRED EMBODIMENT

Figure 1:
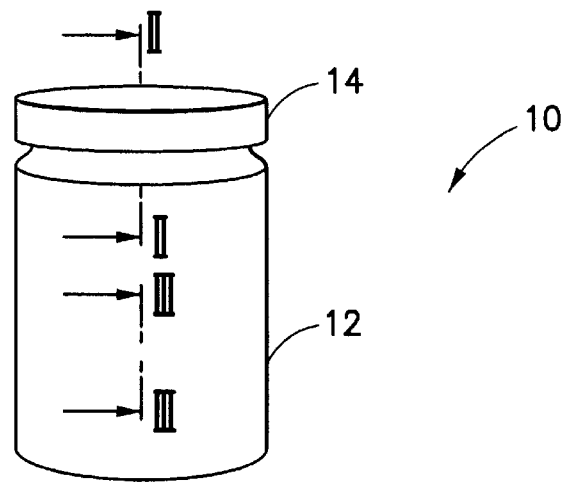
FIG. 1 is a perspective view of an odor collection apparatus according to an embodiment of the present invention.

Referring now to FIG. 1, there is shown, generally at 10, an odor collection apparatus according to an embodiment of the invention. Odor collection apparatus 10 includes a container 12 to which is fittable a sealing cap 14.

Container 12 may be of any convenient material, and may be in any convenient shape. For convenience, container 12 may be glass, so that a conventional glass jelly jar may suffice. For reasons to be discussed hereinafter, container 12 is preferably formed from a metallic material that is good thermal conductor such as, for example, stainless steel. Preferably, container 12 includes generally cylindrical sides, to simplify a coating operation to be described hereinafter.

Figure 2:
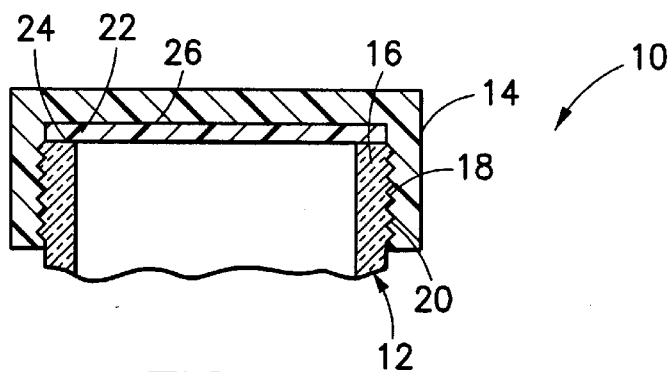
FIG. 2 is a cross section taken along II—II of FIG. 1.

Referring now to FIG. 2, container 12 includes a neck 16 having external threads 18 thereon. Cap 14 includes internal threads 20 that mate with external threads 18. A seal 22 is interposed between an upper lip 24 of container 12 and an inner surface 26 of cap 14. Seal 22 may be of any convenient material such as, for example, a plastic resin, a fluorocarbon such as, for example, Teflon, or metal foil. In many applications, the temperature that can be withstood by container 12 limits the time required to complete the desorption process in preparation for analysis. The higher the temperature tolerated, the faster the desorption. Plastic resins, such as may be used in cap 14, have temperature limits of about 150 degrees C., whereas metals and glasses can tolerate temperatures of 400–600 degrees C. A preferred temperature for efficient desorption of trapped components is about 250 degrees C.

Besides the screw-type seal illustrated for retaining cap 14, other types of seals such as snap-type or lever-type seals may be used without departing from the spirit and scope of the invention.

Figure 3:
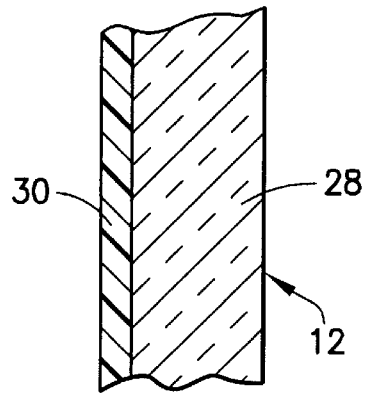
FIG. 3 is a cross section taken along III—III of FIG. 1.

Referring now to FIG. 3, container 12, illustrated as a glass wall 28, is coated on its inside surface with an adsorbent layer 30. Adsorbent layer 30 is formed from any convenient material having suitable adsorbent properties for the odor which one wishes to capture. Prior to coating adsorbent layer 30 on glass wall 28, glass wall 28 is preferably deactivated using, for example, dichlorodimethylsilane.

Adsorbent layer 30, illustrated as a resin material, is any convenient adsorbent, or combination of adsorbents such as polydimethylsiloxane, Carboxen, Tenax, or polydivinylbenzene. Activated carbon may also be used. When a resin is used in adsorbent layer 30, and repeated or cyclic use is desired, the resin may be cross-linked and/or bonded to the surface to stabilize it for resistance to solvent rinsing during cleaning.

The thickness of adsorbent layer 30 influences the quantity of a sample which can be adsorbed, and the rapidity with which the adsorbed material can be desorbed. Without limiting the scope of the invention, the inventor believes that at thicknesses below about one micrometer, insufficient odor components may be adsorbed. Further, the inventor believes that, at thicknesses greater than 1,000 micrometers (one millimeter), the time for desorption may be excessively long. However, thinner and thicker layers should be considered to fall within the scope of the invention.

Referring now to FIG. 4, in some applications, adsorbent layer 30 may consist of successive layers of different materials 30, 30a, 30b, in which different materials are specific to adsorption of different materials. When a plurality of layers is used to make up adsorbent layer 30, all layers may have substantially the same thickness, or some layers may be thicker than others to provide a greater capacity for adsorption.

It would be clear to one skilled in the art that, when a plurality of layers is used to form adsorbent layer 30, the time sequence of materials desorbed during desorption is generally in the order of their position in the stack of layers. That is, the odor components in outermost layer 30b desorb first, while odor components in deeper layers 30a and 30 generally desorb in the sequence of their proximity to the surface. At least one of the layers may be a passive layer which neither sorbs nor desorbs, but merely imposes a delay in the passage of odor components from a deeper layer to the surface. The amount of delay may be related to the type of material in the passive layer, and the thickness of the passive layer.

Referring now to FIG. 5, in some applications, adsorbent layer 30 may be formed into separate zones, 30a, 30b of different adsorbent materials in order to enable storage of a wider range of odor components than is possible with a single material. The separate zones 30a and 30b sorb and desorb in response to the same stimuli, but possibly at different rates due to differences in the affinity of the materials to odor components.

Referring now to FIG. 6, for rapid sorption/desorption cycling, container 12 may be heated by any convenient means. One convenient technique for heating includes conventional electrically resistive tape 32 wrapped about the surface of container 12. An electric cord 34 and an electric plug 36 enable connection to an electrical source. For some purposes, it may be desirable to include a thermostat to maintain the temperature of electrically resistive tape 32 (and thereby the surface of container 12) at a predetermined temperature. The temperature may be fixed, or a thermostat control may be included for setting a desired temperature. A conventional timing device may control the thermostatic control, in order to ensure accurate temperature/time cycling. In a more automated system, a computer control may be employed to produce a desired temperature/time profile which may be required, especially when multiple layers of sorbent material is employed. Such thermostats, timers and computer controls for temperature/time are conventional, and further description thereof is considered unnecessary.

The heating apparatus can take other forms. For example, instead of electrically resistive tape, a moldable, heating-mantle type of soft resistive material may be molded about the outer surface of container 12. Alternatively, a heatable auxiliary container, not shown, that is sized for a tight fit to the outer surface of container 12, may be used to perform the thermal cycling without requiring thermal heating apparatus in container 12 itself. This may be desirable when a large number of containers 12 are to be desorbed. With the auxiliary container, only one container requires the heating ability, rather than the large number of containers 12. This results in improved economy of operation. The auxiliary heating container may contain heat sources of any convenient type such as, for example, electrical resistance wire, steam tubes, etc. In some cases, it may be desirable to heat the interior surface by heating the desorption gas itself, particularly when the container is made of a material that lacks good thermal conductivity.

Between sorption/desorption cycles, it is preferred to clean container 12 by heating for a suitable time at a suitable temperature to fully remove sorbed components. The time and temperature required varies according to the thickness of the sorbent coating in container 12. For one example of container 12, it was found sufficient to heat container 12 for two hours at 200 degrees C.

Numerous methods are available for coating the interior of container 12 with an adsorbent material. Without intending to limit the scope of the present invention, one coating technique is described in the following:

1) deactivate interior surface of 8-ounce glass jar using dichlorodimethyl silane
2) dissolve one gram of solid sorbent material (GE Silicone SE-30) in 100 ml. of solvent (dichloromethane)
3) agitate solvent until sorbent material is dissolved
4) further dilute the mixture in 3) 1:4
5) place 10 ml. of diluted mixture in jar
6) rotate jar on jar mill, with axis of jar horizontal until solvent evaporates
7) cross-link sorbent layer if desired to improve durability during repeated use.

The thickness of the coating deposited in the preceding procedure is controlled by the volume of the sorbent material that is coated on the interior of jar 12. In the above procedure, one gram of material was dissolved into 400 ml of liquid. Ten ml. of the mixture was deposited in the jar, and evaporated to leave only the sorbent material. That is, 1/40th of a gram of the sorbent material was deposited. To double the thickness adsorbent layer 30 requires either doubling the amount of sorbent material dissolved in the solvent, or using twice the amount of adsorbent/solvent mixture added to container before rolling in the jar mill. A simple calculation can be used to reveal the amounts required to produce a specific coating thickness.

One calculation of the amount of adsorbent material required is:

Vessel dimensions:
 Diameter=2.5 inches
 Length=6 inches
 Desired thickness of adsorbent layer=10 $\mu$m
 Area of layer=6×2.5×$\pi$=47.124 in$^2$=304 cm$^2$
 Volume of layer=area×thickness=304 cm$^2$×10 $\mu$m=0.304 cc Assuming that the adsorbent material has a specific gravity of 1.0, then approximately 0.3 grams of adsorbent material must be deposited on the inner surface of container 12 to form adsorbent layer 30.

A device made according to the foregoing method is capable of long-term storage of odor components. For example, an odor sample collected in June was sealed in container 12 as described above. The odor was still strong near the end of August.

Referring now to FIG. 7, when it is desired to collect odor components from living plants such as, for example, a flower 38, which remains attached to its stem 40, a flexible tube 42 may be attached over neck 16 and held in place using, for example, a clamp or rubber band 44. With flower 38 within container 12, a lower end 46 of flexible tube 42 is bunched about stem 40 and secured using, for example a clamp, plastic tie or rubber band 48. After the odor components within container 12 reach equilibrium with the desorption material coating the inner surface of container 12, clamps 44 and 48 are released, and cap 14 (not shown) is replaced over neck 16.

Figure 8:
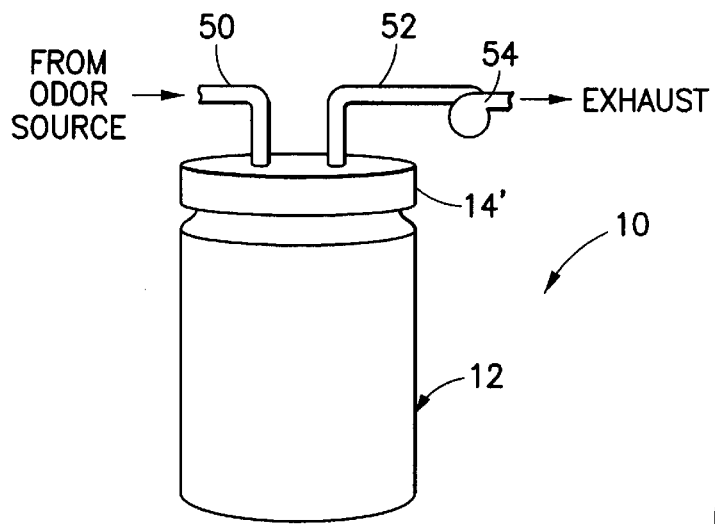
FIG. 8 is a perspective view of an odor collection apparatus in which odor components are delivered by gas flow from an external source.

Referring now to FIG. 8, an alternative embodiment of the invention includes a modified cap 14', pierced by an inlet tube 50 which conducts odor components from an odor source (not shown) into the interior of container 12. An outlet tube 52 conducts the exhaust from container 12 to a pump 54. After a sufficient time of pump operation to enable sorption to be completed, modified cap 14' may be removed, and replaced by cap 14 for long-term storage of the aroma components.

Modified cap 14' may also be used during desorption. That is, when thermal desorption is being performed, modified cap 14' may be installed so that pump 54 is enabled to urge desorbed components, not to the exhaust, but to the analysis apparatus. Inlet tube 50, instead of conducting odor materials, contains a suitable carrier gas such as, for example, helium or hydrogen. The output from pump 54 is fed to conventional analysis apparatus.

When the desorption process takes a long time, or when it is desired to analyze a plurality of separate samples to raise the detection limit of low-level species, the output of pump 54 may be passed initially to a concentration apparatus at the inlet of an analysis apparatus. The concentration may be performed by a conventional cryotrap using, for example, liquid carbon dioxide, liquid nitrogen or a Peltier-effect thermistor. The trapped components are eluted by conventional temperature/pressure programming. If necessary, unresolved components are heart cut and cryotrapped at the inlet of a second gas chromatograph column and eluted a second time for improved identification/quantification.

The size of container 12 is not limited to any particular size range. For example, it may be desired to collect odor from a large object such as, for example, an entire animal or human body, or a part thereof, for possible therapeutic analysis of emitted chemical components. Container 12 may be made large enough to accommodate such a use. Naturally, a source of breathing air, and an exhaust of used breathing air is necessary if the entire body is contained within the container. Conventional aqualung breathing apparatus is suitable for the breathing air supply.

The above disclosure is made in an environment of a cylindrical glass or metal container having an adsorbent material coated on its interior. Although this shape may be convenient, and low cost for many applications, the invention is not limited to such a shape. For example, a flat-sided body may be substituted for the cylindrical shape without departing from the spirit and scope of the invention.

There are many applications in which a flexible container may be more suitable. A flexible container of a suitable resin has the advantage, especially for field work, that it is light, can be folded small for transportation, but can be made with very large capacity. The resin must be of a type which does not contribute significant amounts of its own outgassed chemical components which would interfere with analysis. One suitable type of resin that has been used successfully is flexible plastic resin material sold under the trademark Tedlar. Other suitable flexible plastic resin materials may also be available.

Coating of the interior of the flexible bag is more difficult than the simple rolling of a rigid cylindrical jar in a jar mill. In experiments with a Tedlar bag having a capacity of about one gallon, the diluted adsorbent material was added to the interior of the bag, and the bag was rotated by hand to distribute the diluted adsorbent material roughly equally about the interior. Uniformity of coating is believed to be imperfect using this coating technique. A further problem with the embodiment using a Tedlar bag is determining a method for thermally desorbing chemical components. The techniques described for desorbing with rigid containers is not as applicable to a resilient bag which lacks a rigidly defined shape.

Figure 9:
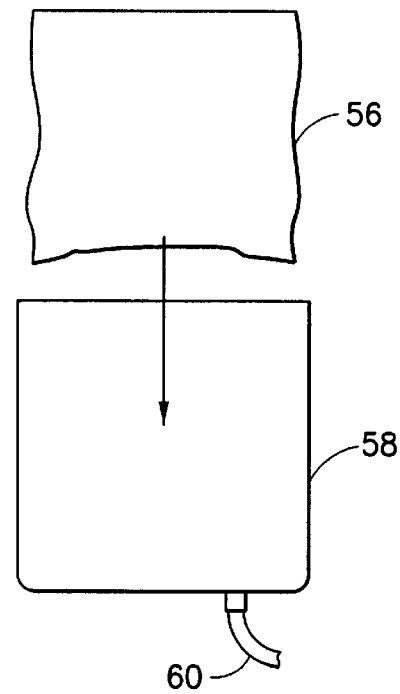
FIG. 9 is a side view of components used in processing a flexible bag to be used for collection of odor components.

Referring now to FIG. 9, a flexible bag 56 of a suitable material, such as Tedlar, is fittable into a rigid container 58. A top of flexible bag 56 is sealed by any convenient means to a top of rigid container 58. A vacuum line 60 connected to the interior of rigid container 58 permits drawing a partial vacuum between flexible bag 56 and rigid container 58, whereby flexible bag 56 is expanded into intimate contact to conform to the interior of rigid container 58. Thus, the interior of flexible bag 56 assumes the generally cylindrical shape of rigid container 58, and can thus accept the same coating steps as were described for the rigid vessels described above. That is, the diluted adsorbent material is introduced into the shaped interior of flexible bag 56 and flexible bag 56 is rotated about its axis, held horizontal, until the diluent evaporates.

In addition to the utility for coating the interior of flexible bag 56, vacuum conforming flexible bag 56 to rigid container 58 also permits rapid heating of flexible bag 56 by conventional heating techniques applied to rigid container 58. After odor components are stored in flexible bag 56, the top may be bunched and sealed by conventional means for retaining the components, and avoiding contamination by environmental chemicals.

Other techniques for coating the interior of a rigid or flexible container may fall within the scope of the invention. For example, the sorbent material, in a suitable solvent, may be sprayed on the interior surface of the container. The thickness of the sorbent layer in this case is controlled by the proportion of sorbent material in the solution, and the nature of the spray. A thicker coating may be obtained with multiple spray coatings, optionally with a drying step between coatings.

Figure 10:
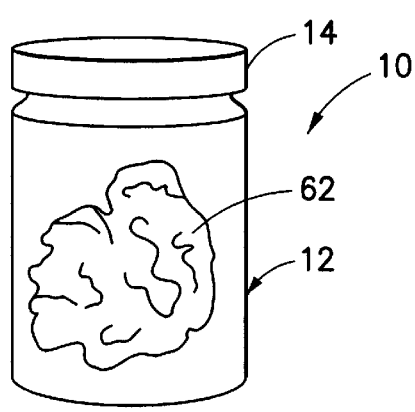
FIG. 10 is a perspective view of an odor collection apparatus in which additional sorbent area is provided by a pleated, folded, curlicue, or porous body within the container.

Referring now to FIG. 10, a further embodiment of the invention includes a large surface-area body 62 within container 12. Large surface-area body 62 may be, for example, a metal or resin fluted body, a perforated body, or other type of device offering a large area upon which the sorbent material may be deposited. One type of material which may be preferred is a stainless steel curly metal pad such as is conventionally used for scrubbing cooking pots. Large surface-area body 62 may be coated with a sorbent material using any suitable method. A preferred method is dipping of large surface-area body 62 into a solution of sorbent material, removing excess sorbent material by shaking or centrifuging, and drying. Multiple coating steps may be used, if necessary. When it is desired to have a plurality of different sorbent materials in the same container, two or more large surface-area bodies 62 may be included. Desorption of odor components from large surface-area body 62 is by conventional means described above. In addition to the sorbent material on large surface-area body 62, the interior of container 12 may also be coated with a sorbent material, as described above, or it may be left uncoated.

One advantage of a system that includes a large surface-area body 62 resides in the fact that large surface-area body 62 may be removable for desorption. Thus, many containers 12 may be used to collect odor components, but only a single device may be necessary to perform the desorption process. The removable large surface-area body 62 may be removed from container 12, and deposited in the desorption device.

The above description discusses heating for desorption using conduction of heat through the walls of the container. Desorption heating by other techniques is fully within the scope of the invention. For example, instead of heat being conducted through the walls of the container, a heated inert gas may be circulated through the container. As a further alternative, desorption heating may employ radiant heating of the surfaces within the container.

The method for coating the interior of the container is not necessarily limited to the flow-coating method described above. An embodiment in which the adsorbent material is coated on the walls of the container or large surface-area body by spray painting, or other suitable techniques, should be considered to fall within the spirit and scope of the invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Apparatus for collecting odor components, comprising:

a container;

means for sealing said container;

a sorbent coating on an interior surface of said container;

said sorbent coating being of a type effective for sorbing odor components; and said container having a capacity sufficient to contain a source of said odor components for a period of time long enough for said odor components to reach equilibrium within said container.

2. Apparatus according to claim 1, wherein said sorbent material is one of a polymer and a polymer mixture.

3. Apparatus according to claim 2, wherein said polymer is stabilized by cross-linking and surface-bonding.

4. Apparatus according to claim 1, wherein said sorbent coating has a thickness from about 1 to about 1,000 micrometers.

5. Apparatus according to claim 1, wherein said sorbent coating includes a plurality of layers of different materials.

6. Apparatus according to claim 5, wherein said plurality of layers are one upon another.

7. Apparatus according to claim 6 wherein an outer one of said plurality of layers retards desorption of odor components from at least one layer below it.

8. Apparatus according to claim 5, wherein at least two of said plurality of layers are in different areas of said container, whereby different odor components may be sorbed.

9. Apparatus according to claim 1, wherein said container is flexible.

10. Apparatus according to claim 9, wherein said container is a Tedlar polymer.

11. Apparatus according to claim 1, wherein said container is substantially rigid.

12. Apparatus according to claim 1, further comprising a heating material on a surface of said container, said heating material being effective to raise a temperature of said sorbent coating to a value effective for desorption of said odor components within a predetermined time.

13. Apparatus according to claim 1, further comprising:

a heater;

said heater including means for permitting insertion temporarily thereinto of said container; and said heater being effective for raising a temperature of said sorbent coating to a value effective for desorption of said odor components within a predetermined time.

* * * * *